United States Patent [19]

Garner

[11] Patent Number: 4,990,858
[45] Date of Patent: Feb. 5, 1991

[54] COAXIAL MICROWAVE ASBORPTION DIAGNOSTIC

[75] Inventor: Harold R. Garner, Encinitas, Calif.

[73] Assignee: General Atomics, San Diego, Calif.

[21] Appl. No.: 357,333

[22] Filed: May 25, 1989

[51] Int. Cl.[5] .................. G01R 27/04; G01R 27/26
[52] U.S. Cl. .................................... 324/639; 324/632; 324/641
[58] Field of Search ...................... 422/98, 62, 63; 324/376, 377, 631, 632, 639, 641, 642

[56] References Cited

U.S. PATENT DOCUMENTS

| | | | |
|---|---|---|---|
| 2,404,797 | 7/1946 | Hansen | 324/641 |
| 4,013,950 | 3/1977 | Falls | 324/642 |
| 4,543,823 | 10/1985 | Nagy | 324/642 |
| 4,626,773 | 12/1986 | Kroeger | 324/642 |
| 4,651,085 | 3/1987 | Sakurai | 324/639 |
| 4,866,371 | 9/1989 | De | 324/639 |

*Primary Examiner*—Kenneth Wieder
*Assistant Examiner*—Jose M. Solis

*Attorney, Agent, or Firm*—Nydegger & Associates

[57] ABSTRACT

A coaxial microwave absorption diagnostic device comprises a hollow cylindrical outer layer conductor with a coaxially aligned conductor rod extending therethrough and a dielectric material which interconnects the outer layer to the conductor rod. The device is formed with a passageway which is directed perpendicular to the longitudinal axis of the device and which passed through the outer layer, the conductor rod and the dielectric material. As so formed, the passageway is positioned for receiving a sample holder, such as a small capillary tube holding a sample solution. A variable or fixed frequency oscillator is electrically connected to an input end of the conductor rod for sending microwave power through the device and a diode senses the output portion of this microwave power which has passed through the device. The absorbed power, i.e. the input microwave power less the output microwave power, is determined by a comparator and used to analyze the sample.

25 Claims, 2 Drawing Sheets

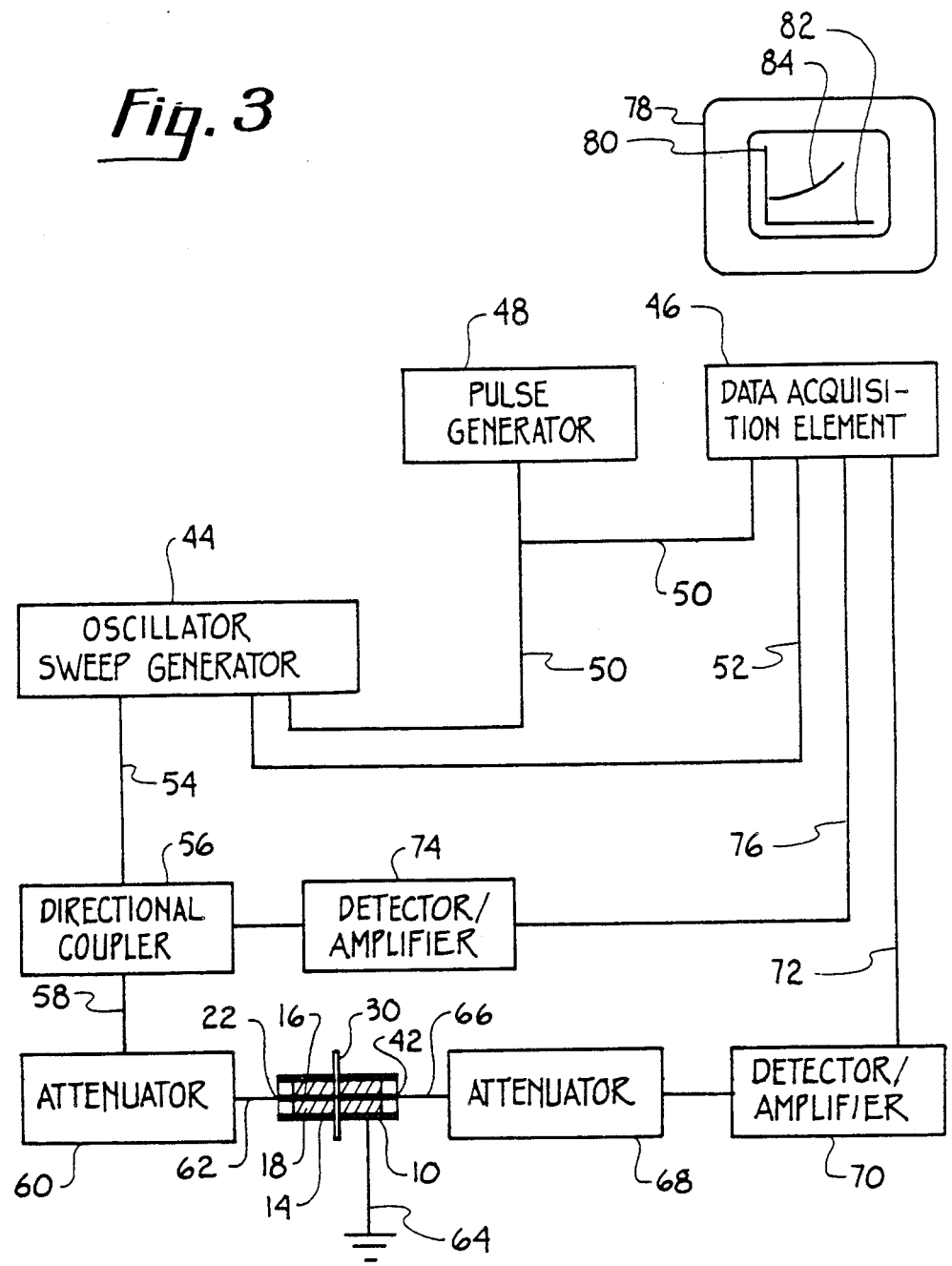

COAXIAL MICROWAVE ASBORPTION DIAGNOSTIC

FIELD OF THE INVENTION

The present invention pertains to diagnostic devices for identifying and analyzing the properties of chemical and biological samples. More particularly, the present invention pertains to diagnostic devices which use microwave power to analyze the chemical and biological properties of agents held in solution. The present invention is particularly, but not exclusively, useful for measuring and analyzing very small quantities of a sample solution.

BACKGROUND OF THE INVENTION

The analysis of a sample solution can be accomplished in several ways. Various procedures, to include chemical analysis of a selected sample, are well known in the pertinent art. Chemical analyses, however, generally exhaust the sample and cannot therefore be used since it is often desirable to neither alter nor destroy the tested sample. This is particularly so when the sample agent in solution is very valuable and only small amounts of the sample are available. In such cases it is preferable to perform nondestructive testing.

It is known that, in many instances, sample solutions have individually identifying characteristics which can be observed without destroying or altering the sample. In general, to perform nondestructive testing it is necessary to subject the sample to a known input and observe the change caused by the sample as manifested by the output. It is, of course, important to precisely identify this input. Knowing the input, it is then simply a matter of accounting for components of this input which are missing from a measured output. In the case of sample solutions, various procedures can be used to determine which components of the predetermined input are absorbed by the sample. For example, it is well known that certain sample solutions absorb particular wavelengths of light in varying degrees of intensity and a spectrophotometer can be used to make use of this fact for the analysis of sample solutions. Light absorption, however, is but one way in which the absorption characteristics of a sample solution can be used to analyze the sample. It is also known that microwave power can be used for this purpose. As with a spectroanalysis, a microwave analysis requires comparison of an output to a known input.

Heretofore, both spectroanalysis and microwave analysis techniques and their attendant procedures have required relatively large sample sizes in order to perform an accurate and precise analysis. This, however, can be a problem when the sample is necessarily very small or is consequently very expensive. Unfortunately, this difficulty is more commonplace now than before due to the increased interest for research in many diverse, highly technical fields of science, e.g., biotechnology. Thus, there is a need for a diagnostic device which can accurately analyze an extremely small sample solution.

The present invention recognizes that sample sizes as small as 0.003 microlitres of solution can be accurately analyzed using microwave technology. Specifically, the present invention recognizes the need for such analysis by a diagnostic device which can measure and analyze a sample solution while it is held in the small capillary tubes that are typically used in research laboratories for handling and transferring minute quantities of sample solutions. The present invention accomplishes this by using a device which incorporates a coaxial geometry.

Theoretically, it has been determined for a diagnostic device having a coaxial geometry that the microwave power absorbed per volume of sample solution can be expressed as:

$$\frac{P_{absorbed}}{V_{sample}} = \frac{\omega \epsilon'' P_{in} R}{(\ln(b/a))^2 ab}$$

where $\omega$ is the microwave radial frequency, $\epsilon''$ is the imaginary part of the dielectric constant, $P_{in}$ is the input microwave power, R is the impedance of the coaxial device, "a" is the outer radius of the inner conductor, and "b" is the inner radius of the outer conductor. Interestingly, this expression neglects reflected power in the device. It happens, however, that with very small sample sizes, and consequently very small sample holders, the reflected power is minimal and is effectively lost within the system noise. Stated differently, with extremely small sample holders, the perturbation to the system which is caused by the sample will be small since proper impedance matching is maintained. Accordingly, for diagnostic purposes, the above expression is acceptably accurate.

In light of the above, it is an object of the present invention to provide a coaxial microwave absorption diagnostic device which is compact and easy to use. Another object of the present invention is to provide a coaxial microwave absorption diagnostic device which is able to measure and analyze extremely small sample solution volumes. Yet another object of the present invention is to provide a coaxial microwave absorption diagnostic device which can analyze a sample solution over a wide range of microwave frequencies. Still another object of the present invention is to provide a coaxial microwave absorption diagnostic device which is reliable and accurate. Another object of the present invention is to provide a coaxial microwave absorption diagnostic device which can be rapidly operated and which is not time consuming. Yet another object of the present invention is to provide a coaxial microwave absorption diagnostic device which is relatively easy to manufacture and which is comparatively cost effective.

SUMMARY OF THE INVENTION

A coaxial microwave diagnostic device for analyzing samples in solution comprises a cylindrical-shaped body formed with a passageway that extends through the body along a line which is substantially perpendicular to the longitudinal axis of the cylinder. A hollow cylindrical-shaped conductor layer establishes the outer surface of the body and a conductor rod is coaxially aligned within the conductor layer. A dielectric material is placed between the outer conductor layer and the conductor rod so that respective portions of the passageway pass sequentially through the outer layer, the dielectric material and the rod.

As intended by the present invention, an oscillator is electrically connected to an input end of the conductor rod to send microwave power through the device. Though there is no effective limitation on the frequencies which can be used by the diagnostic device, preferably, the frequencies of the microwave power generated by the oscillator are in the range of two to twenty-six and one half (2-26.5) GHz and the power level is approximately one (1) milliwatt. A diode is electrically connected to the output end of the conductor rod to detect the microwaves transmitted through the device.

In order to be tested by the coaxial microwave diagnostic device, the sample agent must be inserted into the passage. If solid, the sample is conformed for each insertion. If a liquid or a gas, the sample agent drawn into the capillary of a sample holder. The solid sample or the sample holder with sample agent is then inserted into the passageway of the device and the oscillator is activated to provide a predetermined input to the conductor rod. Electronic components, which may include a microprocessor, are electronically connected to both the oscillator and the output end of the conductor rod to receive and differentiate the microwave input power from the microwave output power in order to determine the microwave power that is absorbed by the sample. A comparator then analyzes the sample using first principles or compares the characteristics of the absorbed power with a known control standard to measure and analyze the sample.

The novel features of this invention, as well as the invention itself, both as to its structure and its operation, will be best understood from the accompanying drawings, taken in conjunction with the accompanying description, in which similar reference characters refer to similar parts, and in which:

BRIEF DESCRIPTION OF THE DRAWINGS

FIG. 3 is a schematic diagram of the electronic components of a system for operating the coaxial microwave absorption diagnostic device.

DESCRIPTION OF THE PREFERRED EMBODIMENT

Figure 1:
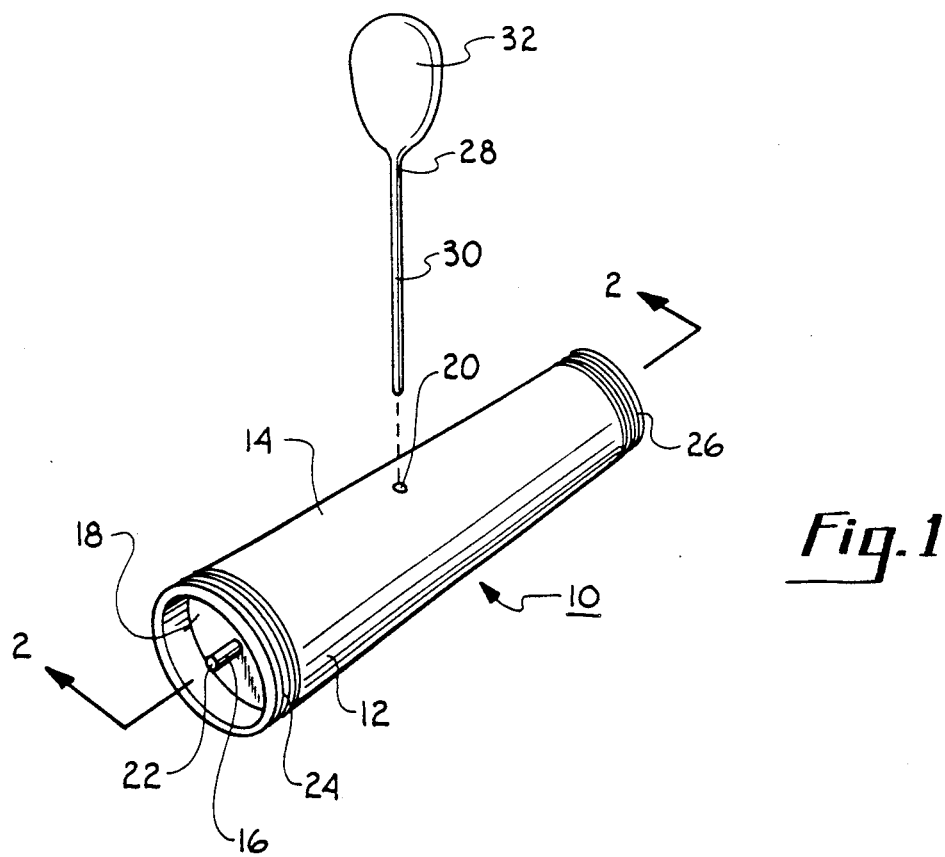
FIG. 1 is a perspective view of the coaxial microwave absorption diagnostic device shown in combination with a sample holder.

Referring initially to FIG. 1, the coaxial microwave absorption diagnostic device of the present invention is shown and generally designated 10. As shown in FIG. 1, device 10 comprises a substantially cylindrical-shaped body 12 which has a conductor outer layer 14 and a coaxially aligned conductor rod 16 which extends substantially along the longitudinal axis of the cylindrical body 12. Outer layer 14 is a substantially hollow cylindrical-shaped component which is electrically conductive in nature. Preferably, outer layer 14 is made of a metal. Similarly, conductor rod 16 is an electrical conductor and is likewise preferably made of a metal. FIG. 1 shows that a dielectric material 18 interconnects conductor rod 16 with outer layer 14 which is preferably made of an insulating material such as Teflon.

A passageway 20 is formed through body 12 such that passageway 20 is directed substantially perpendicular to the longitudinal axis of body 12. As will be better appreciated after subsequent disclosure, passageway 20 passes through outer layer 14, conductor rod 16, and dielectric material 18. FIG. 1 also shows that conductor rod 16 has an input end 22 which extends away from the dielectric material 18. FIG. 1 also shows that outer layer 14 is formed with threads 24 for the purpose of threadably engaging body 12 with an electrical component to be subsequently disclosed. In a similar manner, the end of body 12 opposite input end 22 of conductor rod 16 is formed with threads 26 for a similar purpose.

FIG. 1 also shows a sample holder 28 which is positioned for insertion into passageway 20 of device 10. Specifically, sample holder 28 comprises a capillary tube 30 which is in fluid communication with a bulb 32. As will be appreciated by the skilled artisan, sample holder 28 can be of several varieties well known in the pertinent art. Importantly, however, sample holder 28 should be relatively small and be capable of holding very small quantities of liquid or solid samples. For purposes of the present invention, capillary tube 30 should be capable of holding liquid volumes in solution which are on the order of three thousandths (0.003) microlitres. As intended for the present invention, when capillary tube 30 is inserted into the passageway 20, it will be sequentially positioned against outer layer 14, dielectric material 18 and conductor rod 16. Importantly, the diameter of passageway 20 is kept small in order to provide a tight fit between capillary tube 30 and the sides of passageway 20 in order to avoid distortion of the microwave electric field. Thus, passageway 20 is preferably of a size wherein the diameter of passageway 20 is approximately less than nine tenths (0.9) of a millimeter. In any event, it is important that the passageway 20 be substantially perpendicular to the longitudinal axis of the device 10 and intersect the outer layer 14, conductor rod 16 and dielectric material 18 in a manner substantially as shown. For purposes of the present invention, capillary tube 30 can be made of any material appropriate for use in a microwave environment, such as glass, plastic, Teflon or quartz.

Figure 2:
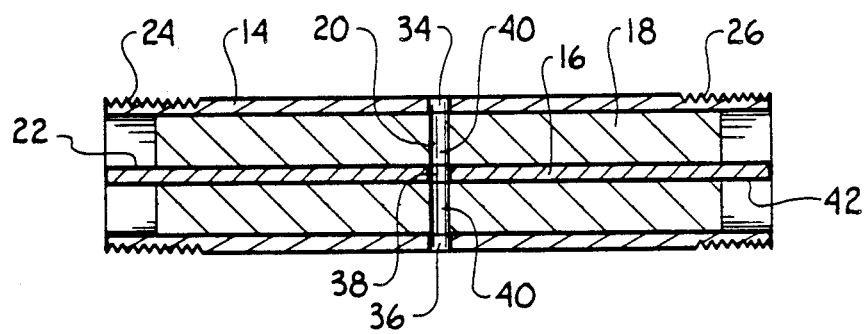
FIG. 2 is a cross-section view of the coaxial microwave absorption diagnostic device as seen along the line 2—2 in FIG. 1.

Referring now to FIG. 2, it will be seen that outer layer 14 is formed with diametrically opposed holes 34 and 36. Additionally, FIG. 2 shows that conductor rod 16 is formed with a transverse hole 38 and that dielectric material 18 is formed with a bore 40. Importantly, transverse hole 38 has a diameter which is less than the outer diameter of conductor rod 16 in order to allow uninterrupted propagation of microwave power along conductor rod 16. As contemplated by the present invention, the alignment with bore 40 of dielectric material 18 of the diametrically opposed holes 34, 36 in outer layer 14, and the transverse hole 38 of conductor rod 16 establishes passageway 20. Additionally, FIG. 2 shows that conductor rod 16 is formed with an output end 42. As will be appreciated by the skilled artisan, device 10 as thus far described, would permit the interchangeability of input end 22 with output 42.

As disclosed above, dielectric material 18 is essentially an insulator. Due to the need for proper impedance matching of device 10 with other electric components of the system to be subsequently disclosed, it may be desirable in an alternate embodiment of the present invention to use a "lossy" material for the dielectric 18. Specifically, a "lossy" dielectric suitable for use with the present invention would preferably be a Teflon, glass or ceramic material impregnated with microwave absorbing materials such as graphite particles, metallic particles, or silicon carbide particles.

Referring now to FIG. 3, it will be seen that the system of electronic components which are necessary for operation of the coaxial microwave absorption diagnostic device 10 are shown in schematic diagram. Specifically, it is seen that an oscillator 44 is provided to generate the microwave power necessary for using device 10 to test sample solutions held in capillary tube 30. Preferably, oscillator 44 is a sweep generator of a type commercially known as a Wiltron 6653a. As shown in FIG. 3, the system also includes a data acquisition element 46 and a pulse generator 48. Further, FIG. 3 shows that pulse generator 48 is electrically connected with oscillator 44 and data acquisition element 46 by a trigger pulse line 50 and a frequency ramped line 52 makes an electrical connection between oscillator 44 and data acquisition element 46. With this circuitry, pulse generator 48 is able to activate oscillator 44 and simultaneously signal data acquisition element 46 that the oscillator 44 is operative. Further, by the connection established by frequency ramp line oscillator 44 indicative of the frequencies being generated by the oscillator 44.

Oscillator 44 is also connected via line 54 with a directional coupler 56. An electrical connection through directional coupler 56 is made by line 58 to an attenuator 60 which is preferably a 10 db attenuator of any type well known in the pertinent art. Attenuator 60 is then electrically connected via line 62 with input end 22 of conductor rod 16. In the operational system for device 10, outer layer 14 of device 10 is grounded by electrical connection 64 and the output end 42 of conductor rod 16 is connected via a line 66 with attenuator 68. Similar to attenuator 60, the attenuator 68 may be of any type well known in the pertinent art and be effective in a range between six (6) and twenty (20) db. It is to be appreciated at this point, that attenuators 60 and 68 are incorporated when dielectric 18 is not a "lossy" dielectric. In the event a "lossy" dielectric 18 is used, both attenuators 60 and 68 may be eliminated. Accordingly, if attenuators 60 and 68 are eliminated and directional coupler 56 is not incorporated, a direct electrical connection between the oscillator 44 and input end 22 of device 10 is possible. This circuit is completed as output end 42 of conductor rod 16 of device 10 is electrically connected through attenuator 68 with a detector/amplifier 70 which transfers a signal proportional to the microwave power output via line 72 to data acquisition element 46.

As mentioned above, the microwave power that is reflected by capillary tube 30 of sample holder 28 is negligible for all practical purposes. If this assumption is made, directional coupler 56 may be eliminated. On the other hand, it may be desirable, or even preferred, to include directional coupler 56 substantially as shown in FIG. 3. When incorporated, directional coupler 56 will detect reflected microwave power from the device 10 and pass it via detector/amplifier 74 and line 76 to data acquisition element 46.

In accordance with the scheme as shown in FIG. 3, data acquisition element 46 receives proper signals from other elements of the system with which it can determine the microwave absorption characteristics of the chemical or biological agent. This is so, regardless whether the agent is a solid or is a gas or liquid held in capillary tube 30. Specifically, data acquisition element 46 obtains a signal from pulse generator 48 which indicates when oscillator 44 is activated. Further, data acquisition element 46 receives a voltage signal via frequency ramp line 52 which is proportional to variations in the microwave frequencies generated by oscillator 44. Preferably, the variation in frequency can be as desired by the operator within the range of two to twenty-six and one half (2-26.5) GHz in order to determine the frequency response absorption over a range of frequencies. As mentioned above, this range of frequencies may be extended. It is possible, however, to test the sample with selected frequencies. Regardless, with this information, data acquisition element 46 receives a signal which identifies the microwave power input to the device 10. Additionally, if incorporated, directional coupler 56 will detect and pass via detector/amplifier 74 and line 76 a signal which is indicative of the microwave power reflected as a standing wave in the device 10. Importantly, via the output end 42 of conductor rod 16, the system transmits a signal to a diode (not shown) in detector/amplifier element 70 and passes a signal along line 72 which indicates the microwave power that has passed through the device 10, i.e. power that has not been absorbed. It is a function then of data acquisition element 46 to correlate the microwave output power signal it receives via line 72 with the frequency sweep signal it receives via line 52 to determine the power that has been absorbed by the chemical or biological sample agent being tested at various frequencies. If desired, this correlation can be further refined by considering any reflected power which might be acquired by data acquisition element 46 via line 76.

A microprocessor (not shown) uses the above data for purposes of determining the power absorbed by the sample in capillary tube 30 for diagnostic purposes. Specifically, the various signals received by data acquisition element 46 can be correlated and transmitted to a display element 78 to provide meaningful information about the sample in capillary tube 30. As can be appreciated by the skilled artisan, the display 78 is able to use signals received by data acquisition element 46 to plot variations in power absorbed 80 relative to changes in frequency 82, such a plot generates a curve 84 that is characteristic of the particular sample agent held in solution in capillary tube 30.

OPERATION

In the operation of the coaxial microwave absorption diagnostic device 10, the sample holder 28 is used to draw a sample solution into capillary tube 30 which contains the chemical or biological agent to be measured and analyzed. Capillary tube 30 is then inserted into passageway 20 of the device 10 to bring capillary tube 30 into contact with the conductor outer layer 14, dielectric material 18 and coaxially aligned conductor rod 16. With sample holder 28 positioned within passageway 20, pulse generator 48 is triggered to activate oscillator 44. This action results in oscillator 44 transmitting a microwave power via line 54, and any other intermediate components, to the input end 22 of conductor rod 16 of device 10. Preferably, oscillator 44 is operated at a power level approximately equal to one (1) milliwatt and the sweep of frequencies in the range of two to twenty-six and one half (2-26.5) GHz is done in approximately one (1) second. It happens that, within these parameters, approximately eight thousand (8000) samples can be taken. The particular characteristics of microwave power generated by oscillator 44 are thus transmitted via frequency ramp line 52 to the data acquisition element 46 for presentation on display 78 as frequency variation 82. Simultaneously, this microwave power is transmitted as input to input end 22 of conductor rod 16 and is then directed through device 10. As intended by the present invention, a portion of the input microwave power to device 10 will be absorbed by the sample agent held in sample holder 28. Indeed, it is this absorbed power which is to be subsequently analyzed to measure characteristics of the sample agent held in device 10. In order to determine this absorbed power, however, it is necessary to compare the output microwave power from device 10 when a sample is positioned in passageway 20 with either the known input microwave power or a measurement of output power without the sample in place. For this purpose, the output from device 10 is transmitted via electrical components from output end 42 of conductor rod 16 to data acquisition element 46. After such a comparison is made by the microprocessor (not shown) in data acquisition element 46, the resultant signal is correlated with frequency 82 and shown on display 78 as curve 84.

While the particular coaxial microwave absorption diagnostic as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

I claim:

1. A diagnostic device for examining a sample which comprises:
   a substantially cylindrical-shaped body defining a longitudinal axis and formed with a passageway substantially perpendicular to said axis for receiving said sample therein, said body comprising an outer conductor layer, a conductor rod having a first end and a second end positioned along said axis, and a dielectric material connecting said layer with said rod to allow a sample holder in said passageway to contact said rod, said dielectric material and said layer;
   means electrically connected with said first end of said rod to propagate a preselected input microwave power through said body along said axis;
   means electrically connected with said second end of said rod for receiving an output microwave power; and
   means for comparing said output microwave power with said input microwave to examine said sample.

2. A diagnostic device for examining a sample as recited in claim 1 wherein said outer conductor layer is grounded.

3. A diagnostic device for examining a sample as recited in claim 1 wherein said outer conductor layer is made of a metal.

4. A diagnostic device for examining a sample as recited in claim 1 wherein said conductor rod is made of a metal.

5. A diagnostic device for examining a sample as recited in claim 1 wherein said dielectric material is Teflon.

6. A diagnostic device for examining a sample as recited in claim 1 wherein said dielectric material is glass.

7. A diagnostic device for examining a sample as recited in claim 1 wherein said dielectric is ceramic.

8. A diagnostic device for examining a sample as recited in claim 1 wherein said means for propagating said preselected input microwave power is an oscillator.

9. A diagnostic device for examining a sample as recited in claim 8 wherein said oscillator is variable to provide input microwave power for said diagnostic device in the range between 2-26.5 GHz.

10. A diagnostic device for examining a sample as recited in claim 1 wherein said dielectric material is microwave absorbing.

11. A diagnostic device for examining a sample as recited in claim 10 wherein said dielectric material is impregnated with microwave absorbing particles.

12. A diagnostic device for examining a sample as recited in claim 11 wherein said microwave absorbing particles are graphite particles.

13. A diagnostic device for examining a sample as recited in claim 11 wherein said microwave absorbing particles are metallic particles.

14. A diagnostic device for examining a sample as recited in claim 11 wherein said microwave absorbing particles are silicon carbide particles.

15. A diagnostic device for examining a sample as recited in claim 1 wherein said receiving means is a diode.

16. A diagnostic device for examining a sample as recited in claim 1 further comprising a first attenuator electrically connecting said input microwave power propagating means with said first end of said conductor rod and a second attenuator electrically connecting said receiving means with said second end of said conductor rod for damping standing waves in said diagnostic device.

17. A diagnostic device for examining a sample as recited in claim 1 wherein said passageway is approximately less than nine tenths (0.9) mm in diameter.

18. A diagnostic device for examining a sample which comprises:
   a hollow cylindrical conductor defining a longitudinal axis and having a pair of diametrically opposed holes formed therethrough;
   a conductor rod having a first end and a second end and coaxially positioned along said axis within said cylindrical conductor, said rod being formed with a transverse hole extending across said axis;
   a dielectric material connecting said conductor rod to said cylindrical conductor and having a bore therethrough alignable with said hole in said rod and said holes in said cylindrical conductor to establish a passageway for receiving said sample;
   means electrically connected with said first end of said rod to propogate a preselected input microwave power through said body along said axis;
   means electrically connected with said second end of said rod for receiving an output microwave; and
   means for comparing said output microwave with said input microwave to examine said sample.

19. A diagnostic device for examining a sample as recited in claim 18 wherein said means for propagating said preselected input microwave power is an oscillator.

20. A diagnostic device for examining a sample as recited in claim 19 wherein said oscillator is variable to provide input microwave power for said diagnostic device in the range between 2-26.5 GHz.

21. A diagnostic device for examining a sample as recited in claim 18 wherein said receiving means is a diode.

22. A diagnostic device for examining a sample as recited in claim 18 wherein said passageway is approximately less than nine tenths (0.9) mm in diameter.

23. A method for examining agents which comprises the steps of:
   engaging a sample agent with a diagnostic device which comprises a substantially cylindrical shaped body defining a longitudinal axis and formed with a passageway substantially perpendicular to said axis for receiving said sample agent therein, said body comprising an outer conductor layer, a conductor rod having a first end and a second end positioned along said axis and a dielectric material connecting said layer with said rod to allow said sample agent in said passageway to contact said rod, said dielectric and said layer;

electrically connecting said first end of said conductor rod with a means for generating microwave power input;

electrically connecting said second end of said conductor rod with a means for detecting the microwave power transmitted through said diagnostic device;

activating said generating means; and comparing said microwave power detected by said detecting means with said input microwave power to determine predetermined properties of said agents.

24. A method for examining sample agents as recited in claim 23 further comprising the step of varying the frequency of microwave power input in the range 2–26.5 Hz.

25. A method for examining sample agents as recited in claim 23 wherein said comparing step is accomplished first without a sample agent and subsequently with a sample agent.

* * * * *

UNITED STATES PATENT AND TRADEMARK OFFICE
CERTIFICATE OF CORRECTION

PATENT NO. : 4,990,858

DATED : February 5, 1991

INVENTOR(S) : Harold R. Garner

It is certified that error appears in the above-identified patent and that said Letters Patent is hereby corrected as shown below:

In the title of the patent "ASBORPTION" should be changed to read "ABSORPTION".

In column 1, line 1, "ASBORPTION" should be change to read "ABRORPTION".

Signed and Sealed this

Thirtieth Day of June, 1992

Attest:

DOUGLAS B. COMER

Attesting Officer

Acting Commissioner of Patents and Trademarks